United States Patent [19]

Usui et al.

[11] Patent Number: 5,378,831

[45] Date of Patent: Jan. 3, 1995

[54] GALACTOSYL MALTOOLIGOSACCHARIDE DERIVATIVES

[75] Inventors: Taichi Usui, Shizuoka; Osamu Uejima, Mishima; Koichi Ogawa, Fuji, all of Japan

[73] Assignees: Nihon Shokuhin Kako Co., Ltd.; Yaizu Suisan Kagaku Kogyou Co., Ltd.

[21] Appl. No.: 941,302

[22] Filed: Sep. 4, 1992

[51] Int. Cl.$^6$ .................. C07G 17/00; C07G 3/00; C07H 1/00; C08B 37/00
[52] U.S. Cl. .................. 536/123.1; 536/4.1; 536/17.8; 536/18.4
[58] Field of Search .................. 536/4.1, 123, 123.1

[56] References Cited

U.S. PATENT DOCUMENTS

| | | | |
|---|---|---|---|
| 4,857,640 | 8/1989 | Henkel et al. | 536/4.1 |
| 4,963,479 | 10/1990 | Chavez et al. | 536/4.1 |

FOREIGN PATENT DOCUMENTS 0080442  6/1983  European Pat. Off. ............ 536/4.1

OTHER PUBLICATIONS

Usui et al (1992) Analytic Biochemistry 202, pp. 61–67.
Usui et al (1996) Japan Data Base Abstract Accession No. 91-264596.
Ogawa et al (1990) Agric Biol Chem, 54, pp. 581–586.
Usui et al (1988) J. Biochem 103, pp. 969–972.

*Primary Examiner*—Douglas W. Robinson
*Assistant Examiner*—Jeffrey J. Sevigny
*Attorney, Agent, or Firm*—Burns, Doane, Swecker & Mathis

[57] ABSTRACT

Galactosyl maltooligosaccharide derivatives represented by formula (1):

wherein at least one of $X_1$ and $X_2$ represents a galactosyl group and the other represents a hydrogen atom, R represents a hydrogen atom or a substituted or unsubstituted phenyl group, and n is an integer of from 2 to 5. The derivatives are prepared by reacting a sugar with a galactosyl group with a maltooligosaccharide represented by formula (2):

R represents a hydrogen atom or a substituted or unsubstituted phenyl group, and n is an integer of from 2 to 5; in the presence of α-galactosidase or β-galactosidase. The derivatives are used for measurement of α-amylase activity.

7 Claims, 2 Drawing Sheets

GALACTOSYL MALTOOLIGOSACCHARIDE DERIVATIVES

BACKGROUND OF THE INVENTION

1. Field of the Invention

The present invention relates to novel galactosyl maltooligosaccharide derivatives with excellent steerage stability which can be used as a substrate for measurement of α-amylase activity. The present invention further relates to a method for preparation of the above derivatives and a method for measurement of α-amylase activity using the derivatives.

2. Description of the Related Art

It is quite important for clinical diagnosis to measure the activity of α-amylase contained in body fluids of humans such as saliva, pancreatic carcinoma or parotitis, especially when these levels are remarkably increased. Therefore, the α-amylase activity is an important indicator for clinical diagnosis.

Among of various substrates for assay methods of α-amylase activity reported previously, maltooligosaccharides and their derivatives having definite chemical structures are widely used these days.

In most of these methods, enzyme activity is determined by measuring glucose or adsorption value of various aglycons (e.g., p-nitrophenol), which are liberated from maltooligosaccharides or their derivatives by the simultaneous action of α-amylase and coupled enzymes (α-and/or β-glucosidases) during the reaction, respectively.

However, it is very difficult to keep the initial quality of these substrates at a constant level, during preservation when the mixture of the coupled enzyme and substrate is stored as a solution, because these coupled enzymes have the ability to hydrolyze the substrates even if these preparation are sufficiently free from α-amylase activity. In order to improve the conventional methods, it has been tried to use some substrates, which are obtained by chemical modification of the nonreducing end of glucose of the maltooligosaccharides or their derivatives, to prevent hydrolysis by these coupled enzymes during preservations.

These kinds of chemically modified substrates are not hydrolyzed by coupled enzymes such as α-D-glucosidase and glucoamylase.

Accordingly, it is possible to obtain a stable preparation containing substrate and the coupled enzyme for the assay of α-amylase activity. These substrates prevent the significant increase of blank value even if they are preserved for a long time.

For example, methods using nonreducing end substituted maltooligosaccharides with a carboxymethyl group and 2-pyridylamino residue as a substrate are known (see Japanese Patent Disclosure No.59-31699 (JP-A-31699/1984), No. 59-51800(JP-A-51800/1984) and 61-83195 (JP-A-83195/1986)). However, complicated steps are required for the preparation of these kinds of substrates. For instance, after random chemical modification of glucose molecules in dextrin or amylose, the partially modified macromolecular saccharides are hydrolyzed with bacterial saccharifying type α-amylase and glucoamylase to obtain nonreducing end substituted maltooligosaccharides, and the resulting maltooligosaccharides are further fractionated in a certain chromatographic fractionated manner with certain kinds of resins to prepare modified maltooligosaccharides having definite a degree of polymerization. Then, these nonreducing end substituted maltooligosaccharides are transferred to certain acceptors such as p-nitrophenyl α-D-glucoside with cyclomaltodextrin glucanotransferase to obtain maltooligosaccharides of which both terminal glucose molecules are modified. And, the resulting product both reducing-and nonreducing-end substituted maltooligosaccharides are fractionated further by chromatographic methods to obtain the modified saccharides having a definite chemical structure and molecular mass. Due to these complicated procedures for preparation, the yield of the desired derivatives is low and therefore, this method is impractical.

There have been many patents regarding the assay method for α-amylase activity using maltooligosaccharide derivatives of which the nonreducing end glucose molecule was chemically modified, and the opposite end glucose was linked to some kinds of chromophore (see Japanese Patent Disclosure No.60-54395 (JP-A-54935/1985), No.60-87297(JP-A-87297/1985), No.60-237998(JP-A-237998/1985), No.61-3299(JP-A-63299/1986), No.63-301892(JP-A-301892/1988) and No.1-157996(JP-A-157996/1989)).

In these methods, a substituent in such as benzylidene, ethylidene, iso-propylidene, halogen, alkyl, phenyl, benzyl or ketobutyl is introduced into the nonreducing end glucose of a maltooligosaccharide and the products are used as substrates. However, the chemical synthesis methods in which the nonreducing end is specifically modified require complicated steps, for example, an acetylation and a deacetylation step is required and therefore the yield of the final products is low.

As mentioned above, preparation of maltooligosaccharide derivatives with the modified nonreducing end glucose is difficult, and also it is not easy to use them practically as a substrate for the assay of α-amylase activity.

An object of the invention is to provide novel maltooligosaccharide derivatives which are easy to prepare and stable against the coupled enzymes when they are used as a substrate for the assay method of α-amylases activity.

A further object of the invention is to provide a process for preparation to the above novel maltooligosaccharide derivatives and a method for measurement of the activity of α-amylase.

SUMMARY OF THE INVENTION

The present invention relates to a galactosyl maltooligosaccharide derivative represented by formula (1):

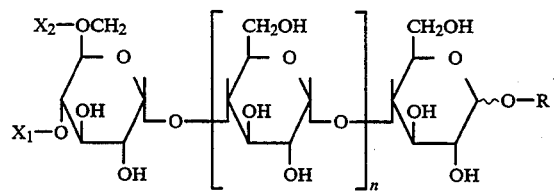

wherein at least one of $X_1$ and $X_2$ represents a galactosyl group and the other represents a hydrogen atom, R represents a hydrogen atom or a substituted or unsubstituted phenyl group, and n is an integer of 2 to 5.

Figure 1:
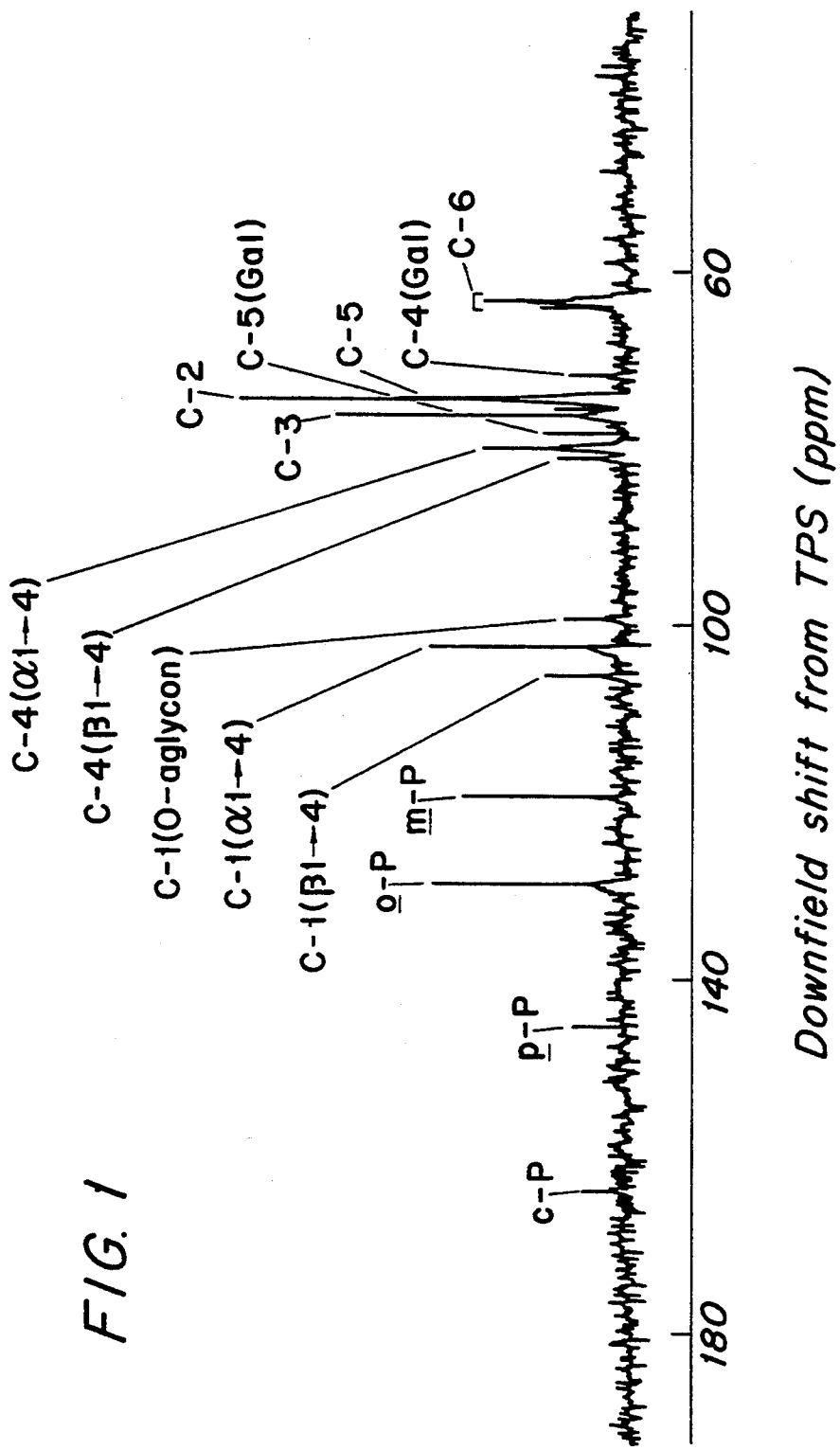
FIG. 1 shows a $^{13}$CNMR spectrum of pNP-α-G5(Gal)1 of the invention.

The present invention will be explained below:

In formula (1), one of $X_1$ and $X_2$ is a galactosyl group or both of $X_1$ and $X_2$ are galactosyl groups. When one of $X_1$ and $X_2$ is a galactosyl group, the other is a hydrogen atom. The substituted phenyl group represented by R may be selected from some groups which release a chromophore by the reaction of glucoamylase, α-glucosidase or β-glucosidase, such as 4-nitrophenol, 2-chloro-4-nitrophenol and 2,4-dichlorophenol.

The linkage of an aglycon to the glycoside may take either α-form or β-form.

In formula (1), n is an integer of 2 to 5. n is preferably 3 or 5, taking into consideration of water solubility as the substrate.

The above novel maltooligosaccharides are obtained by a novel process using a transfer reation of an enzyme. In this process, the galactosyl transfer reaction between a sugar with a galactosyl group, a donor, and a maltooligosaccharide, an acceptor, is conducted by the use of α- or β-galactosidase to synthesize objective novel maltooligosaccharides.

The process of the invention will be explained below:

The sugar with a galactosyl group is represented by formula (3):

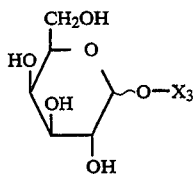

In the formula, $X_3$ represents a glucose group, a sucrose group or a oligomer of galactose.

Examples of the sugar with a galactosyl group include lactose, melibiose, raffinose, stachyose and galactooligosaccharides. The sugar is preferably a disaccharide such as lactose or melibiose, and especially lactose is preferred in industrial production because it is inexpensive.

The maltooligosaccharide derivative used as an acceptor is represented by formula (2):

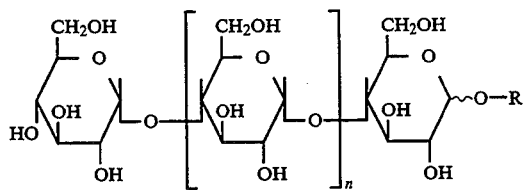

In the formula, the definition of R is the same as that of formula (1) and n is an integer 2 to 5.

Examples of the compounds (2) include maltooligosaccharides (R=H) such as maltotetraose, maltopentaose, maltohexaose and maltoheptaose. Examples of the compounds of which R is a phenyl group include phenyl-α-maltoside, phenyl-α-trioside, phenyl-α-tetraoside, phenyl-α-pentaoside, phenyl-α-hexaoside and phenyl-α-heptaoside. Examples of the compounds of which R is a substituted phenyl group include p-nitrophenyl-α-maltoside, p-nitrophenyl-α-trioside, p-nitrophenyl-α-pentaoside, p-nitrephenyl-α-hexaoside and p-nitrephenyl-α-heptaoside.

α-and β-galactosidase used in the invention are known enzymes which hydrolyze the galactosidic linkage to release galactose. In the invention, β-galactosidases is used when β-galactoside such as lactose is used as a donor and α-galactosidase is used when α-galactoside such as melibiose or raffinose is used as a donor. Regardless of origin, any kind of β-galactosidases may be used in the invention. Examples are Biolacta (available from Daiwa kasei in Japan), Lactase F "Amano" (available from Amano Seiyaku in Japan), Lactase Y-AO (available from Yakult in Japan) and Lactase P (KI Kasei in Japan). Any kind of α-galactosidases, regardless of its origin, may be used. Examples of the α-galactosidase include α-galactosidaes originated from *Mortierella vinacea* and *Absidia reflexa* (available from Hokkaido Togyo in Japan) and α-galactosidase originated from Green Coffee Beans (available from Sigma).

The galactosyl transfer reaction by the enzyme of the invention is preferably performed in a solvent. Examples of the solvent include water and a mixed solvent of water and a hydrophilic organic solvent. The use of the mixed solvent is preferred since the yield of the objective product is increased.

Any hydrophilic organic solvent may be used and examples of the solvent include dimethylsulfoxide, dimethyl formamide, n-propanol, iso-propanol, acetone, methanol, ethanol, ethylene glycol and propylene glycol. The solvent may be used solely or a mixture of two or more solvents may be used.

The content of the hydrophilic organic solvent in the mixed solvent may be varied depending on the kind of the solvent and ranges from about 10 to 70%, preferably 20 to 60%.

In the galactosyl transfer reaction of the invention, the substrate concentration of the sugar with a galactosyl group suitably ranges from 10 to 40% and the substrate concentration of maltooligosaccharide derivative (2) suitably ranges from 10 to 40%. The reaction period suitably ranges from about 5 to 40 hours. The reaction temperature suitably ranges from 20° to 60° C. After completion of the reaction, the enzymic reaction is stopped by adjusting the pH or heating, and the reaction products are fractionated by, for example, chromatographic manners to obtain maltooligosaccharide derivative (1) of the invention. The column chromatography is conducted with, for example, Toyopearl HW-40S gel (available from TOSOH CORPORATION in Japan) using 25% methanol solution as a mobile phase or by an ODS column (available from YMC CORPORATION in Japan) using 10% methanol solution as a mobile phase. It is possible to recover unreacted maltooligosaccharides or maltooligosaccharide derivatives and recycle them to the glucosyl transfer reaction to remarkably increase the yield of the reaction.

The thus obtained maltooligosaccharide derivative (1) is used as a substrate for measurement of the α-amylase activity. Any samples containing α-amylase may be measured and examples of the sample used as an enzyme source include blood, serum, urine and saliva of human. Glucoamylase, α-glucosidase, β-glucosidase or a mixture thereof is used as a coupling enzyme. Any coupling enzymes originated from microorganisms, plants and the like may be used. The activity of α-amylase may be measured under the same conditions as those employed in the conventional methods using a maltooligosaccharide derivative as a substrate. For instance, the concentration of the substrate preferably ranges from about 0.1 to 10 mM. The reaction temperature preferably ranges from about 25° to 40° C. The reaction temperature may be varied depending on the purpose of the measurement and usually ranges from about 3 to 30 minuts. The suitable pH ranges from about 6 to 8 and the pH is adjusted by using a buffer solution.

The present invention will be illustrated in detail in reference to the following examples.

EXAMPLES

EXAMPLE 1

Lactose 209.5 mg (122.4 mM) and p-nitrophenyl-α-maltopentaoside (pNP-α-G5) 290.5 mg (61.2 mM) were dissolved in 1 ml of 20 mM phosphate buffer solution (pH 7.0) containing 20% (v/v) dimethylsulfoxide. One mg of β-galactosidase (Trade name: BIOLACTA available from Daiwa Kasei in Japan) was added to the resulting solution and the solution was allowed to stand at 40° C. for 18 hours whereby 16% of pNP-α-G5, a substrate, was transferred to p-nitrophenyl-α-galactosyl-maltopentaoside (pNP-α-G5(Gal)). After completion of the reaction, fractionation was conducted by using a column ($\phi$2.2×95 cm) charged with Toyopearl HW-40s gel (available from TOSOH CORPORATION in Japan) (mobile phase: 25% methanol, flow rate: 0.8 ml/min, temperature: room temperature) to obtain the ritented fraction.

The fraction was freeze-dried to obtain 40 mg of powder. The powder was a mixture of compounds in which a galactosyl group was bonded to the nonreducing terminal glucosyl group in β-1,4 form and in β-1,6 form (production ratio: β-1,4:β-1,6=about 4:1). The mixture was factionated by an ODS column (YMC-pach AQ-323) (mobile phase: 10% methanol, flow rate: 3.8 ml/min, room temperature) and freeze-dried to obtain 25 mg of a compound in which a galactosyl group was bonded to the nonreducing terminal glucosyl group in β-1,4 form. $^{13}$C nuclear magnetic resonance spectrum of the product was measured and assured that the galactosyl group was bonded to the nonreducing terminal glucosyl group. The results of the NMR is shown in FIG. 1.

EXAMPLE 2

In order to investigate a time course change of the blank value of a reagent, 100 U/ml of yeast α-glucosidase and 5 mg of a substrate were added to 1.0 ml of 0.1M 3,3-dimethylglutaric acid-5M NaOH buffer solution (pH 6.8) containing 0.04M of $CaCl_2$. The absorbance change at 405 nm of the solution kept at 30° C. was measured time-coursely. pNP-α-G5(Gal) of the present invention obtained in Example 1 was used as the substrate and pNp-α-G5 was used for comparison. The results are shown in Table 1.

TABLE 1

| | Absorbance at 405 nm | | |
|---|---|---|---|
| | 0 min | 45 min | 60 min |
| pNP-α-G5 (Gal) | 0.029 | 0.030 | 0.030 |
| pNP-α-G5 | 0.037 | 0.246 | 0.320 |

EXAMPLE 3

Figure 2:
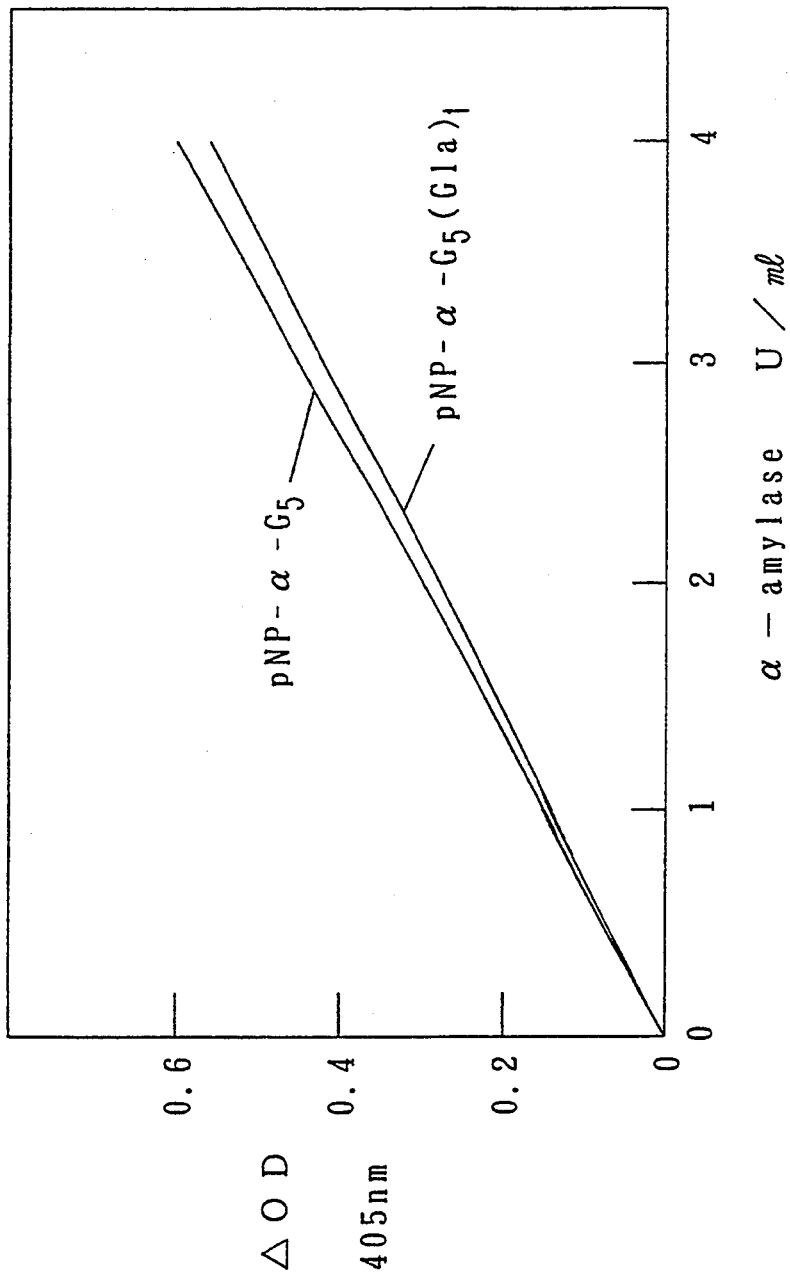
FIG. 2 shows the relation between the concentration of α-amylase and absorption differences obtained by the use of pNP-α-G5(Gal)1 and pNP-α-G5.

In order to study a change in absorbance caused by α-amylase, 5 mg of a substrate and 40 U/ml of yeast α-glucosidase in addition to α-amylase obtained from the pancreas of a pig were added to 1 ml of 50 mM phosphate buffer solution containing 10 mM of NaCl and the absorbance at 405 nm was measured at 37° C. for 20 min. pNP-α-G5 (Gal) of the invention obtained in Example 1 and pNP-═-G5 were used as the substrate. The above α-amylase was added to the solution so as to adjust the concentration at 1 U/ml, 2 U/ml, 3 U/ml or 4 U/ml. The results are illustrated in FIG. 2. The mutual relation between the α-amylase activity and the absorbance is clearly showed from FIG. 2. It was also recognized that a difference in the change in absorbance between pNP-α-G5 (Gal) and pNP-α-G5 is small.

When the galactosyl maltooligosaccharide derivative of the present invention is used as the substrate, the increase of the blank value caused by α-glucosidase, a coupling enzyme, at measurement of the α-amylase activity is inhibited, and the measurement can be performed in the same manner as that of the conventional method. It is possible to prepare a solution containing a substrate and a coupling enzyme(s) such as α-glucosidase and glucoamylase in advance and store the solution. This means that the substrate of the present invention is quite useful for a measurement of the α-amylase activity.

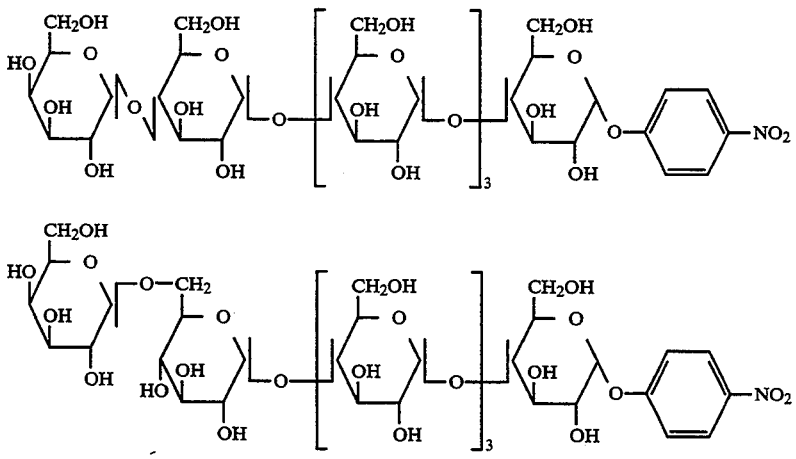

Further, a process for preparation of the galactosyl maltooligosaccharide derivatives of the invention can use lactose which is inexpensive. The process uses a relatively simple enzymic reaction, and the yield is good. Thus the process is suitable for industrial production.

The method for measurement of the activity of α-amylase can be applied to the wide-range measurement of the activity of α-amylase contained in a human body fluid as same as those of the conventional methods.

What we claim is:

1. A galactosyl maltooligosaccharide derivative represented by formula (1):

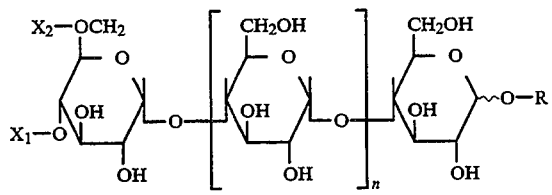

wherein at least one of $X_1$ and $X_2$ represents a galactosyl group and the other represents a hydrogen atom, R represents a hydrogen atom or a substituted or unsubstituted phenyl group, and n is an integer of from 2 to 5.

2. The galactosyl maltooligosaccharide of claim 1 wherein $X_1$ represents a galactosyl group, $X_2$ represents a hydrogen atom and R represents a substituted phenyl group.

3. The galactosyl maltooligosaccharide of claim 2 wherein the substituted phenyl group is selected from the group consisting of p-nitrophenyl, 2-chloro-4-nitrophenyl and 2,4-dichlorophenyl.

4. The galactosyl maltooligosaccharide of claim 2 wherein n is an integer of 3 or 5.

5. A galactosyl maltooligosaccharide of claim 1 wherein $X_1$ represent a hydrogen atom, $X_2$ represents a galactosyl group and R represents a substituted phenyl group.

6. The galactosyl maltooligosaccharide of claim 5 wherein the substituted phenyl group is selected from the group consisting of p-nitrophenyl, 2-chloro-4-nitrophenyl and 2,4-dichlorophenyl.

7. The galactosyl maltooligosaccharide of claim 5 wherein n is an integer of 3 or 5.

* * * * *